US00PP36535P2

(12) United States Plant Patent
Kordes

(10) Patent No.: US PP36,535 P2
(45) Date of Patent: Mar. 11, 2025

(54) MINIATURE ROSE PLANT NAMED 'KORpot129'

(50) Latin Name: *Rosa hybrida*
Varietal Denomination: KORpot129

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/400,205

(22) Filed: Dec. 29, 2023

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./121
See application file for complete search history.

(56) References Cited

PUBLICATIONS https://online.plantvarieties.eu/publicConsultationDetails?registerId=20232113&denomination=Korpot129 (Retrieved online Jul. 1, 2024) (Year: 2023).*

* cited by examiner

*Primary Examiner* — Shubo (Joe) Zhou
*Assistant Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot129', is described. The new variety forms in abundance on a substantially continuous basis pink-colored double, rosette blossoms. The vegetation is semi-glossy and dark green. A compact growth habit is displayed. Ornamental foliage is formed.

1 Drawing Sheet

Latin name of genus and species of plant claimed: *Rosa hybrida.*

Variety denomination: 'KORpot129'.

STATEMENT REGARDING PRIOR DISCLOSURES BY THE INVENTOR

The first offer for sale of the new variety was February 2023 in the EU. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of miniature rose plant of the present invention was created by controlled breeding in 2019 in Offenseth-Sparrieshoop, Germany by artificial pollination wherein two parents were crossed which previously had been studied in the hope that they would contribute the desired characteristics. The female parent (i.e., the seed parent) of the new variety was an unnamed seedling (not patented). The male parent (i.e., the pollen parent) of the new variety was a different unnamed seedling (not patented) which was the product of the cross between 'KORpot010' (not patented) and 'RUId244a' (not patented).

The parentage of the new variety can be summarized as follows:

unnamed seedling x ('KORpot010' x 'RUId244a')

The seeds resulting from the above pollination were sown and small plants were obtained which were physically and biologically different from each other. Selective study resulted in the identification of a single plant of the new variety.

The new variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of miniature rose plant of the present invention possesses the following combination of characteristics:

(a) forms pink-colored blossoms,
(b) exhibits a compact growth habit, and
(c) provides semi-glossy, dark green vegetation.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the variety of the present invention can be readily distinguished from the unnamed female parent (i.e., the seed parent), in that the present invention displays a higher petal count and smaller flower size compared to the seed parent. Additionally, the new variety provides a harder petal structure and a more compact growth habit compared to the unnamed male parent (i.e., the pollen parent). Moreover, the new variety can be readily distinguished from non-parental related similar varieties. For example, 'KORpot042' (U.S. patent application Ser. No. 14/544,576, application abandoned) displays a lighter pink colored flower (Red-Purple Group 65A at the center of the flower, and Red-Purple Group 65A to 65B towards the outer whorls) compared to the new variety.

The new variety has been named the 'KORpot129' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately sixteen weeks of age and was grown indoors on its own roots in a 10.5 cm container in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a one-year-old specimen of the new variety, observed during September, while growing in a one-gallon container on its own roots in a greenhouse in Cochranville, Pennsylvania.

Botanical classification: *Rosa hybrida* cultivar 'KORpot129'.

Commercial classification: Miniature Rose.

Plant:

*Habit*.—Compact.

*Height*.—Approximately 40.0 cm on average from the top of the soil plane in a 1-gallon container.

*Width*.—Approximately 30.0 cm on average.

Branches:

*Stem color*.—Green Group 143C.

*Length*.—Main stems: approximately 40.0 cm on average. Secondary stems: approximately 20.0 cm on average.

*Diameter*.—Main stems: approximately 6.0 mm on average. Secondary stems: approximately 3.0 mm on average.

*Texture*.—Glabrous.

*Prickles*.—Young prickles: amount is moderate; length is approximately 4.0 mm on average; width is approximately 1.0 mm on average at point of attachment; and color is Greyed-Red Group 178B. Old prickles: amount is moderate; length is approximately 7.0 mm on average; width is approximately 4.0 mm on average at point of attachment; and color is Greyed-Green Group 197A.

Leaflets:

*Number*.—3, 5, and 7.

*Shape*.—Ovate; apex is acute; and base is rounded.

*Arrangement*.—Odd-pinnate.

*Margin*.—Serrate.

*Glossiness of upper side*.—Semi-glossy.

*Texture*.—Upper surface: smooth. Under surface: smooth.

*Venation pattern*.—Reticulate.

*Size*.—Terminal leaflet: length is approximately 5.0 cm on average; width is approximately 3.0 cm on average. Lower leaflets: length is approximately 3.2 cm on average; width is approximately 2.5 cm on average. 5-Leaflet leaf: length is approximately 10.5 cm on average; width is approximately 7.0 cm on average.

Foliage:

*Young foliage*.—Upper surface color: Yellow-Green Group 144A edged in Red Group 53B with indistinguishable venation. Under surface color: Green Group 143C and Greyed-Purple Group 185B with venation of Green Group 143C.

*Old foliage*.—Upper surface color: Green Group 141B with indistinguishable venation. Under surface color: Green Group 138B and with indistinguishable venation.

*Petiole*.—Texture: upper surface has sparse prickles; under surface is mostly smooth with intermittent prickles. Length: approximately 2.5 cm on average. Width: approximately 2.0 mm on average. Upper surface color: Green Group 143A. Under surface color: Green Group 143C.

*Rachis*.—Length: approximately 1.7 cm on average. Width: approximately 1.0 mm on average. Upper surface color: Green Group 143A. Under surface color: Green Group 143C.

*Stipules*.—Length: approximately 8.0 mm on average. Width: approximately 3.0 mm on average. Margin: entire to erose. Upper surface color: Yellow-Green Group 144B. Lower surface color: Yellow-Green Group 144A.

Inflorescence:

*Number of flowers*.—About 7 to 10 blooms on average on a plant at once.

*Number of blossoms per stem or in a cluster*.—Typically 1 to 4 blooms per stem on average.

*Peduncle*.—Color: Green Group 143A. Diameter: approximately 3.0 mm on average. Length: approximately 3.5 cm on average. Surface texture: hispidulous.

*Sepals*.—Number: 5. Upper surface color and texture: Green Group 138A and Green Group 138B, covered in short pubescence. Under surface color and texture: Green Group 138A, puberulent. Size: length is approximately 2.8 cm on average; width is approximately 5.0 mm on average. Margin: entire with occasional extensions on two or three sepals measuring approximately 7.0 mm in length and 2.0 mm in width on average with moderate/medium undulation. Shape: lanceolate. Apex: acute to aristate. Base: truncate or flat as it joins the receptacle.

*Buds*.—Shape: globular. Size: length is approximately 2.0 cm on average; width is approximately 2.0 cm on average. Color (when opening): Red Group 54B mixed with Red Group 54C.

*Flower*.—Form: double, rosette. Profile: flat. Diameter: approximately 7.0 cm on average. Height: approximately 3.0 cm on average. Duration: on the plant approximately 20 days. Petal color when first and fully opened: upper surface is Red-Purple Group 58D with a basal spot of Yellow Group 9A; under surface is Red Group 55A with a basal spot of Yellow Group 9B. Petal color at end of bloom: upper surface is Red Group 55B with a hint of Red Group 55C; under surface is Red Group 55B with a hint of Red Group 55C. Petals reflex one by one: yes.

*Fragrance*.—Very light sweet fragrance.

*Petal*.—Number: 70 on average. Drop: average for the type. Length: inner petals typically 2.1 cm; outer petals typically 3.3 cm. Width: inner petals typically 1.5 cm; outer petals typically 3.1 cm. Overall shape: broadly obovate. Margin: entire with medium undulation. Apex shape: rounded to cuspidate. Base shape: rounded to cuneate. Texture: upper surface is glabrous; under surface is glabrous.

*Petaloids*.—Number: approximately 5. Length: approximately 1.1 cm on average. Width: approximately 4.0 mm on average. Color: upper and under surfaces are Red Group 55A with a basal spot of Yellow Group 6B. Texture: smooth. Margin: variable, entire to erose. Shape: rounded and mostly curving inward. Apex: rounded. Base: cuneate.

*Stamen*.—Number: approximately 40. Anthers: number is approximately 40; color is Greyed-Yellow Group 161A; length is approximately 2.0 mm on average; and shape is oval. Filaments: length is approximately 6.0 mm on average and color is Yellow Group 13A.

*Pistils*.—Arrangement: separate and free. Number: approximately 60. Style: length is approximately 6.0 mm and color is White Group 155C at the base, transitioning to Red Group N45B at the apex. Stigma: diameter is less than 1.0 mm on average; shape is fan shaped; color is Yellow-Green Group 145D.

*Receptacle*.—Diameter: approximately 7.0 mm on average. Shape: urn shaped. Color: Yellow-Green Group 144B. Surface texture: smooth.

*Pollen*.—None observed.

*Hips/seed*.—None observed.

Development:

*Vegetation*.—Dark green.

*Blossoming*.—Abundant and continuous; blooms may continue year-round if grown inside a warm greenhouse.

*Resistance to diseases*.—Good resistance for powdery mildew (*Sphaerotheca pannosa*) under normal greenhouse growing conditions in Cochranville, Pennsylvania.

*Hardiness*.—Unknown.

The new 'KORpot129' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot129' characterized by the following combination of characteristics:

(a) forming attractive, pink-colored blossoms, (b) exhibiting a compact growth habit, and (c) providing semi-glossy, dark green vegetation;

substantially as herein shown and described.

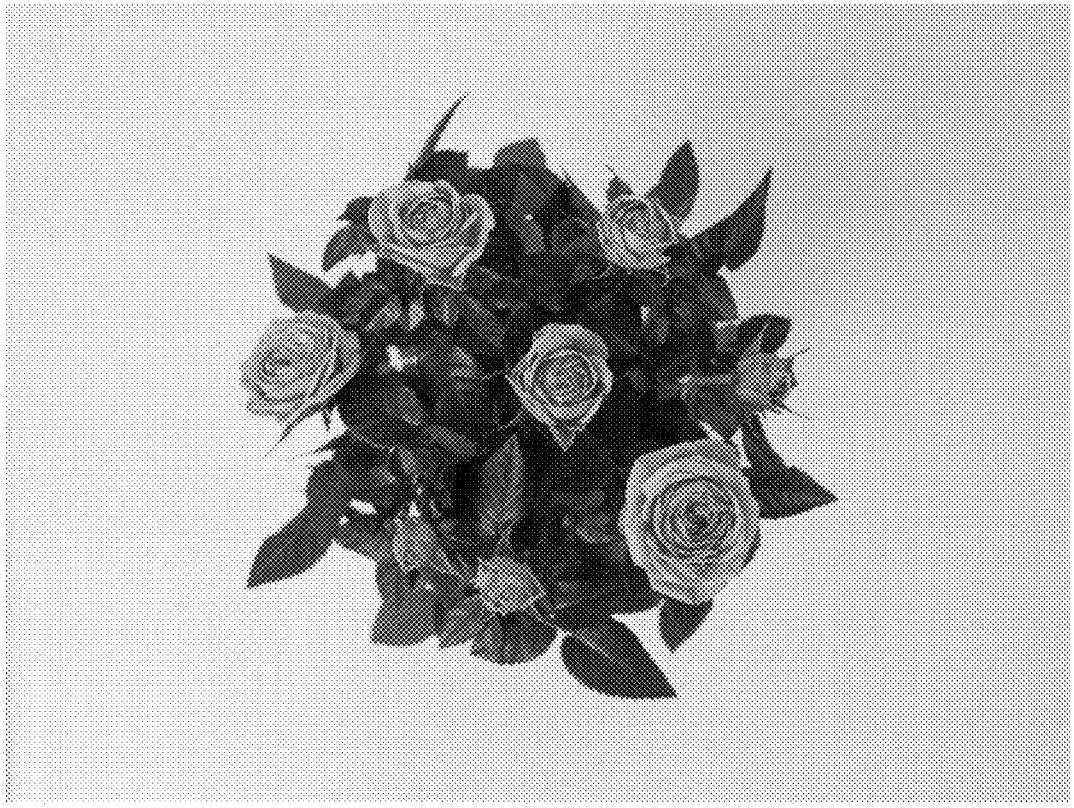

* * * * *